US009589364B2

(12) United States Patent
Park et al.

(10) Patent No.: US 9,589,364 B2
(45) Date of Patent: Mar. 7, 2017

(54) ULTRASOUND IMAGING APPARATUS AND METHOD OF CONTROLLING THE SAME

(71) Applicant: SAMSUNG ELECTRONICS CO., LTD., Suwon-si (KR)

(72) Inventors: Sungchan Park, Suwon-si (KR); Yun-tae Kim, Hwaseong-si (KR); Youngihn Kho, Seoul (KR); Kyuhong Kim, Seoul (KR); Baehyung Kim, Yongin-si (KR); Jungho Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 13 days.

(21) Appl. No.: 14/824,252

(22) Filed: Aug. 12, 2015

(65) Prior Publication Data

US 2016/0055650 A1 Feb. 25, 2016

(30) Foreign Application Priority Data

Aug. 19, 2014 (KR) .................. 10-2014-0107732

(51) Int. Cl.
*G06T 7/20* (2006.01)
*G06T 7/00* (2006.01)
(Continued)

(52) U.S. Cl.
CPC .......... *G06T 7/2006* (2013.01); *A61B 8/0866* (2013.01); *A61B 8/0883* (2013.01); *A61B 8/466* (2013.01); *A61B 8/483* (2013.01); *A61B 8/5223* (2013.01); *A61B 8/5246* (2013.01); *A61B 8/5276* (2013.01); *G01S 15/8977* (2013.01);
(Continued)

(58) Field of Classification Search
CPC .. G06T 5/00; G06T 5/001; G06T 5/50; G06T 7/0012; G06T 7/0083; G06T 7/0097; G06T 7/20; G06T 7/2006; G06T 19/20; G06T 2207/10132; G06T 2207/10136; G06T 2207/30044; G06T 2207/30048; G01S 15/8977; G01S 15/8993; A61B 8/0858; A61B 8/0866; A61B 8/0883; A61B 8/483; A61B 8/5276
See application file for complete search history.

(56) References Cited

U.S. PATENT DOCUMENTS

2008/0226128 A1* 9/2008 Birtwistle et al. ............ 382/103
2011/0075885 A1* 3/2011 Yuan ............................ 382/106
(Continued)

*Primary Examiner* — Andrew W Johns
(74) *Attorney, Agent, or Firm* — Sughrue Mion, PLLC

(57) ABSTRACT

Disclosed herein are an ultrasound imaging apparatus and a method for controlling the same. An occluded region generated in a 2D image may be removed by performing frame interpolation on a surface region of an object by extracting the surface region of the object from 3D ultrasonic volume data and calculating a motion vector in the extracted surface region, and an amount of calculation may be reduced by calculating a motion vector of the surface region in 3D volume data. The ultrasound imaging apparatus includes a volume data generator configured to acquire volume data which relates to the object, a surface region extractor configured to extract the surface region of the object based on the acquired volume data, and a frame interpolator configured to perform frame interpolation on the extracted surface region of the object.

20 Claims, 15 Drawing Sheets

(51) Int. Cl.
*G06K 9/46* (2006.01)
*A61B 8/08* (2006.01)
*G06T 19/20* (2011.01)
*G01S 15/89* (2006.01)
*G06T 3/40* (2006.01)
*A61B 8/00* (2006.01)

(52) U.S. Cl.
CPC ............ *G01S 15/8993* (2013.01); *G06K 9/46* (2013.01); *G06T 3/4007* (2013.01); *G06T 7/0012* (2013.01); *G06T 7/0083* (2013.01); *G06T 7/0097* (2013.01); *G06T 19/20* (2013.01); *A61B 8/0808* (2013.01); *A61B 8/4405* (2013.01); *A61B 8/488* (2013.01); *G06T 2207/10081* (2013.01); *G06T 2207/10116* (2013.01); *G06T 2207/10132* (2013.01); *G06T 2207/10136* (2013.01); *G06T 2207/30024* (2013.01); *G06T 2207/30044* (2013.01); *G06T 2207/30048* (2013.01); *G06T 2207/30104* (2013.01); *G06T 2207/30196* (2013.01); *G06T 2210/41* (2013.01); *G06T 2211/40* (2013.01)

(56) References Cited

U.S. PATENT DOCUMENTS

2012/0075638 A1* 3/2012 Rollins et al. ................ 356/479
2014/0185923 A1* 7/2014 Chen et al. ........ G06K 9/00523
382/154

* cited by examiner

SURFACE EXTRACTION

ULTRASOUND IMAGE AT A TIME OF t

ULTRASOUND IMAGE AT A TIME OF t+1

ULTRASOUND IMAGING APPARATUS AND METHOD OF CONTROLLING THE SAME

CROSS-REFERENCE TO RELATED APPLICATION(S)

This application claims priority from Korean Patent Application No. 10-2014-0107732, filed on Aug. 19, 2014 in the Korean Intellectual Property Office, the disclosure of which is incorporated herein by reference in its entirety.

BACKGROUND

1. Field

Exemplary embodiments relate to ultrasound imaging apparatuses performing frame interpolation only on a surface region of a 3D ultrasound image by extracting the surface region and methods for controlling the same.

2. Description of the Related Art

Ultrasound diagnostic apparatuses non-invasively generate an image of a target region inside an object, such as a soft tissue tomogram or a blood stream tomogram, by irradiating ultrasonic signals generated by transducers of a probe toward the target region from the surface of the object, and receive reflected ultrasonic signals (ultrasonic echo signals), which are used for medical purposes, for example, to examine the inside of the object, detect impurities, and measure injury.

Since ultrasound diagnostic apparatuses are small and inexpensive, display an image in real time, and provide high safety without causing X-ray exposure, as compared to other diagnostic imaging apparatuses, such as X-ray diagnosis apparatuses, computed tomography (CT) scanners, magnetic resonance imaging (MRI) apparatuses, and nuclear medicine diagnosis apparatuses, the ultrasound diagnostic apparatus have been widely used with other diagnostic imaging apparatuses.

With the recent expansion of use of ultrasound systems, various requirements for ultrasound images provided by the ultrasound systems are continuously increasing. In particular, since precise examination of lesions and tissues of patients are required for medical treatments such as examination, biopsy, and surgery, ultrasound systems must be able to acquire multifocal ultrasound images.

However, when a multifocal ultrasound image is acquired, a frame rate of the ultrasound image provided by an ultrasound system may considerably decrease. Accordingly, in a medical treatment requiring real time ultrasound images, natural ultrasound images cannot be provided.

In addition, it is difficult to acquire natural ultrasound volume images of a fetus due to a low frame rate.

Thus, a technique of increasing the number of frames and frame rate is used by frame interpolation. In this regard, when frame interpolation is performed on a 2D image by using a motion vector, an occluded region that is hidden by motion or movement of the fetus may be generated. Although all tissues may be identified via a 3D image without causing an occluded region when volume interpolation is performed on 3D volume data by using a motion vector, an amount of calculation increases due to calculation of a motion vector of V*V*V from a volume of N*N*N.

Thus, there is a need to develop a method of performing frame interpolation by calculating a motion vector without causing an occluded region to reduce the amount of calculation.

SUMMARY

Therefore, it is an aspect of one or more exemplary embodiments to provide an ultrasound imaging apparatus and a method for controlling the same. An occluded region caused when using a 2D image may be removed by performing frame interpolation in a surface region of an object by extracting the surface region of an object from 3D ultrasound volume data and calculating a motion vector of the surface region. An amount of calculation may be reduced by calculating a motion vector of the surface region of 3D volume data.

Additional aspects of the exemplary embodiments will be set forth in part in the description which follows and, in part, will be apparent from the description, or may be learned by practice of the exemplary embodiments.

In accordance with one aspect of one or more exemplary embodiments, an ultrasound imaging apparatus includes a volume data generator configured to acquire volume data which relates to an object, a surface region extractor configured to extract a surface region of the object based on the acquired volume data, and a frame interpolator configured to perform frame interpolation on the extracted surface region of the object based on the calculated motion vector.

The ultrasound imaging apparatus may further include a motion vector calculator configured to calculate a motion vector in the extracted surface region of the object.

The motion vector calculator may include an occluded region motion vector calculator configured to calculate a motion vector of an occluded region.

The occluded region may include a region which corresponds to a time difference between a first predetermined time and a second predetermined time in the surface region of the object.

The occluded region may include a region generated when the frame interpolation is performed.

The motion vector calculator may be further configured to calculate the motion vector by comparing volume data which relates to the first predetermined time with volume data which relates to the second predetermined time.

The occluded region motion vector calculator may be further configured to calculate the motion vector of the occluded region simultaneously with calculating the motion vector in the surface region of the object.

The motion vector calculator may include a surface region and motion vector tracker configured to track a surface region and a motion vector of a predetermined frame.

The surface region and motion vector tracker may be further configured to track the surface region and the motion vector of the predetermined frame based on data which relates to the extracted surface region and the calculated motion vector.

The motion vector calculator may be further configured to calculate a motion vector of a subregion of a frame.

The surface region extractor may be further configured to extract a surface region of at least one from among an outline of a fetus and an organ such as a heart.

In accordance with another aspect of one or more exemplary embodiments, a method for controlling an ultrasound imaging apparatus includes acquiring volume data which relates to an object, extracting a surface region of the object based on the acquired volume data, and performing frame interpolation on the extracted surface region of the object.

The method may further include calculating a motion vector in the extracted surface region of the object.

The calculating the motion vector on the extracted surface region of the object may include calculating a motion vector of an occluded region.

The occluded region may include a region which corresponds to a time difference between a first predetermined time and a second predetermined time in the surface region of the object.

The occluded region may be generated when the frame interpolation is performed.

The calculating the motion vector in the surface region of the object may be performed by calculating a motion vector by comparing volume data which relates to the first predetermined time with volume data which relates to the second predetermined time.

The calculating the motion vector of the occluded region may be performed simultaneously with calculating the motion vector in the surface region of the object.

The calculating the motion vector in the surface region of the object may include tracking a surface region and a motion vector of a predetermined frame.

The tracking the surface region and the motion vector of the predetermined frame may be performed by tracking a surface region and a motion vector of the predetermined frame based on data which relates to the extracted surface region and the calculated motion vector.

The object may include a fetus, and the extracting the surface region of the object may be performed by extracting a surface region of at least one from among an outline of the fetus and an organ such as a heart.

The calculating the motion vector of the surface region of the object may be performed by calculating a motion vector of a subregion of a frame.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
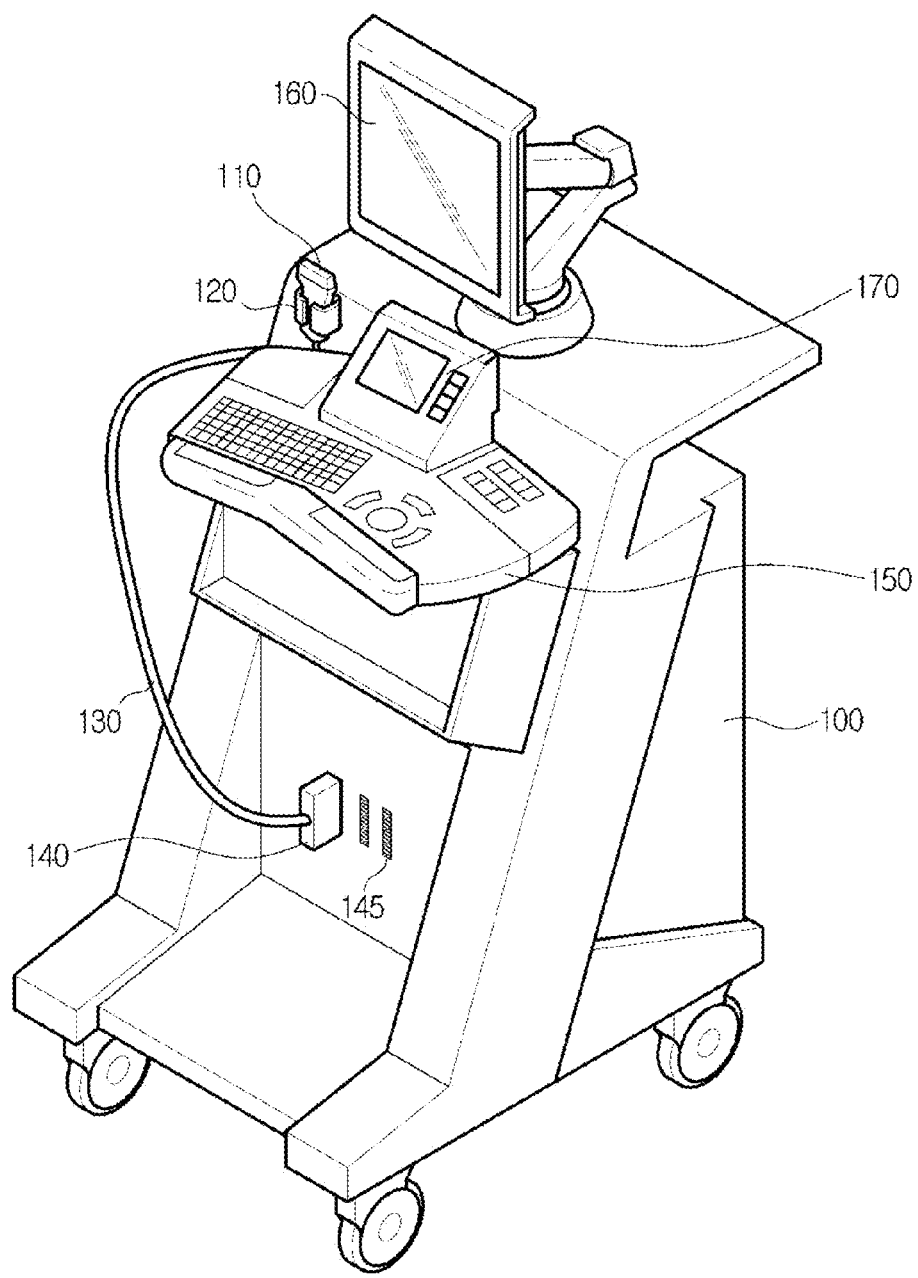
FIG. 1 is a perspective view illustrating an ultrasound imaging apparatus, according to an exemplary embodiment.

Reference will now be made in detail to exemplary embodiments of the present disclosure, examples of which are illustrated in the accompanying drawings, wherein like reference numerals refer to like elements throughout.

Hereinafter, an ultrasound imaging apparatus and a method for controlling the same will be described in detail with reference to the drawings.

A medical imaging apparatus according to an exemplary embodiment may refer to any one or more of an X-ray imaging apparatus, a fluoroscopic X-ray system, a computed tomography (CT) scanner, a magnetic resonance imaging (MRI) apparatus, a positron emission tomography apparatus, and an ultrasound diagnostic apparatus. Hereinafter, an ultrasound imaging apparatus will be described as a medical imaging apparatus by way of example. As used herein, the term 'ultrasound image' refers to an image of an object acquired using ultrasound. As used herein, the term object" refers to human, fetus, animal, metal, non-metal, or a part thereof. For example, the object ob may include any one or more of organs such as liver, heart, uterus, brain, breast, and abdomen and/or blood vessels. In addition, the object may also include a phantom. Phantom refers to a material that has density, effective atomic number, and volume similar to biological tissues.

As used herein, the term "user" refers to medical professionals such as doctors, nurses, medical laboratory technologists, medical imaging professionals, ultrasound examiners, medical equipment technicians, and the like, without being limited thereto.

FIG. 1 is a perspective view illustrating an ultrasound imaging apparatus, according to an exemplary embodiment. Referring to FIG. 1, the ultrasound imaging apparatus includes a main body 100, an ultrasound probe 110, an input unit (also referred to herein as an "input device") 150, and a display 160.

The main body 100 may be provided with at least one female connector 145 at one side thereof. A male connector 140 connected to a cable 130 may be physically coupled to the female connector 145.

Meanwhile, a plurality of casters (not shown) may be provided at the bottom of the main body 100 in order to enable the ultrasound imaging apparatus to move. The plurality of casters may fix the ultrasound imaging apparatus at a predetermined place or allow the ultrasound imaging apparatus to move in a predetermined direction. Such ultrasound imaging apparatuses are referred to as cart-type ultrasound imaging apparatuses.

Alternatively, the ultrasound imaging apparatus may be a portable ultrasound imaging apparatus that may be carried during a long distance journey, as opposed to that illustrated in FIG. 1. In this regard, the portable ultrasound imaging apparatus may not be provided with casters. Examples of the portable ultrasound imaging apparatus may include any of a picture archiving and communication system (PACS) viewer, a smart phone, a laptop computer, a personal digital assistant (PDA), and a tablet PC, without being limited thereto.

The ultrasound probe 110 that contacts the surface of the body of an object may transmit and receive ultrasonic signals. In particular, the ultrasound probe 110 may transmit ultrasonic signals into the object in accordance with a signal received from the main body 100, receive ultrasonic echo signals reflected by a specific region of the object, and transmit the received ultrasonic echo signals to the main body 100.

One end of the cable 130 may be connected to the ultrasound probe 110, and the other end of the cable 130 may be connected to the male connector 140. The male connector 140 connected to the other end of the cable 130 may be physically coupled to the female connector 145.

Alternatively, differently from FIG. 1, the ultrasound probe 110 may be wirelessly connected to the main body 100. In this case, the ultrasound probe 110 may transmit the ultrasonic echo signals received from the object to the main body 100 in a wireless manner. In addition, a plurality of ultrasound probes may be connected to one main body.

Meanwhile, an image processor 350 that converts ultrasonic echo signals received by the ultrasound probe 110 into an ultrasound image may be mounted in the main body 100. The image processor 350 may be implemented as at least one of a hardware processor, such as a microprocessor, and/or as a software processor executed on a hardware platform.

The image processor may generate an ultrasound image via scan conversion of ultrasonic echo signals. In this regard, the ultrasound image may include not only a gray scale image acquired by scanning the object in an amplitude mode (A mode), a brightness mode (B mode), and a motion mode (M mode), but also a Doppler image representing an image of a moving object by using the Doppler Effect. The Doppler image may include any of a blood stream Doppler image indicating a flow of blood (color Doppler image), a tissue Doppler image showing movement of tissues, and a spectrum Doppler image illustrating a speed of a moving object as waveforms.

The image processor may extract B mode components from the ultrasonic echo signals received by the ultrasound probe 110 in order to generate a B mode image.

Similarly, the image processor may extract Doppler components from the ultrasonic echo signal in order to generate a Doppler image in which motion of the object is expressed as color or waveforms based on the extracted Doppler components.

Furthermore, the image processor may generate a 3D ultrasound image by performing volume rendering of volume data acquired by the ultrasonic echo signal, or may generate an elastic image in which the degree of deformation of the object by pressure is imaged. In addition, the image processor may express additional information on the ultrasound image by using texts and graphics.

Meanwhile, the generated ultrasound image may be stored in at least one of an internal memory of the main body and/or an external memory. Alternatively, the ultrasound image may also be stored in a web storage or a cloud server.

The input unit 150 may receive an instruction related to operation of the ultrasound imaging apparatus. For example, the input unit 150 may receive an instruction to select a mode such as the A mode, the B mode, the M mode, or the Doppler image mode. The input unit 150 may also receive an instruction to initiate an ultrasonic diagnosis.

The instruction input via the input unit 150 may be transmitted to the main body 100 via a wireless or wired communication network.

The input unit 150 may include at least one of a keyboard, a foot switch, and/or a foot pedal. The keyboard may be a hardware element located at an upper portion of the main body 100. The keyboard may include at least one of a switch, a key, a joystick, and a trackball. As another example, the keyboard may include a software element, such as a graphical user interface. In this case, the keyboard may be displayed via a sub display 161 or a main display 162. The foot switch or foot pedal may be provided at a lower portion of the main body 100, and a user may control operation of the ultrasound imaging apparatus by using the foot pedal.

The display 160 may include the main display 161 and the sub display 162.

The sub display 162 may be provided at the main body 100. FIG. 1 illustrates that the sub display 162 is provided on the input unit 150. The sub display 162 may display an application related to operation of the ultrasound imaging apparatus. For example, the sub display 162 may display any of menus, guidelines, or the like for ultrasonic diagnosis. Examples of the sub display 162 may include cathode ray tubes (CRTs) and liquid crystal displays (LCDs).

The main display 161 may be provided at the main body 100. FIG. 1 illustrates that the main display 161 is provided above the sub display 162. The main display 161 may display an ultrasound image acquired during the ultrasonic diagnosis in accordance with an input applied via the input unit. The main display 161 may also include a CRT or a LCD similarly to the sub display 162. Although FIG. 1 illustrates that the main display 161 is coupled to the main body 100, the main display 161 may also be separately formed from the main body 100.

FIG. 1 illustrates that the ultrasound imaging apparatus includes both the main display 161 and the sub display 162. However, the sub display 162 may not be used. In this case, applications or menus displayed on the sub display 162 may be displayed on the main display 161.

Meanwhile, the ultrasound imaging apparatus may further include a communication unit (also referred to herein as a "communicator" and/or as a "transceiver"). The communication unit communicates with an external device or a server in a state of being connected in a wired or wireless network. The communication unit may transmit/receive data to/from a server of a hospital or a medical apparatus in the hospital connected via a picture archiving and communication system (PACS). In addition, the communication unit may perform data communication via the Digital Imaging and Communications in Medicine (DICOM).

The communication unit may perform transmission and reception of data related to diagnosis of the object such as an ultrasound image, an ultrasonic echo signal, and Doppler data via a network, and may also perform transmission and reception of medical images acquired by another medical apparatus such as a CT scanner, an MRI apparatus, and an X-ray apparatus. Moreover, the communication unit may receive information related to medical history or treatment schedule of a patient from the server to diagnose a disease of the object. Furthermore, the communication unit may perform data communication with a portable terminal of a doctor or a patient, in addition to the server or medical apparatus of the hospital.

The communication unit may transmit/receive data to/from a portable terminal in a wired or wireless network. The communication unit may include one or more elements enabling communications with external apparatuses, for example, a short distance communication module, a wired communication module, and a wireless communication module.

The short distance communication module is a module which is configured for communicating with a device located within a predetermined distance. A short distance communication technology according to an exemplary embodiment may include any of a wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), and/or the like without being limited thereto.

The wired communication module is a module which is configured for communicating by using an electric signal or an optical signal, and a wired communication technology according to an exemplary embodiment may include any of wired communication technology using a pair cable, a coaxial cable, an optical fiber cable, and an Ethernet cable.

The mobile communication module may transmit/receive a wireless signal to/from at least one of a base, an external terminal, and a server in a mobile communication network. Here, the wireless signal may include any of a voice call signal, a video call signal, or various types of data according to text/multimedia messages transmission.

Figure 2:
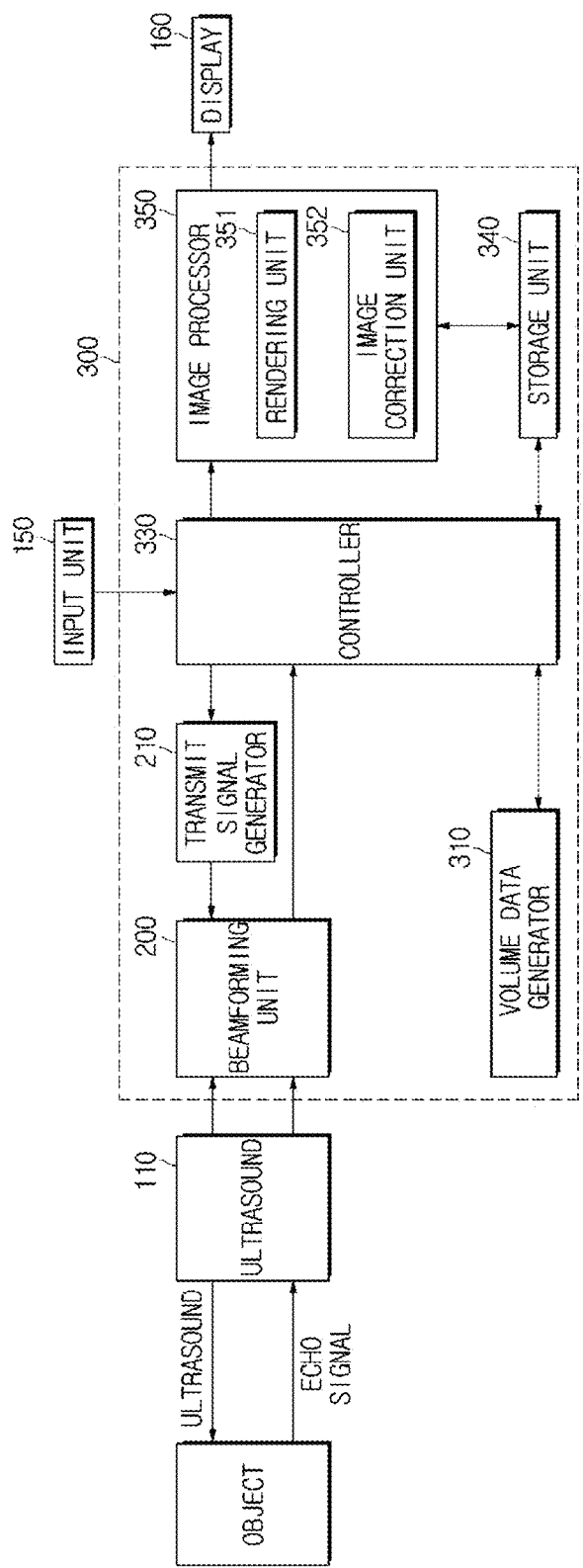
FIG. 2 is a control block diagram illustrating an ultrasound imaging apparatus, according to an exemplary embodiment.

FIG. 2 is a control block diagram illustrating an ultrasound imaging apparatus, according to an exemplary embodiment.

The ultrasound probe 110 includes a plurality of transducer elements to perform interconversion between electrical signals and ultrasonic signals and may transmit ultrasonic signals to an object and receive echo signals reflected by the object. Since ultrasound reflectivity varies according to medium, the ultrasound probe 110 may acquire information which relates to the inside of the object by collecting ultrasonic echo signals.

The ultrasound probe 110 may be implemented in any of various ways within the technical concept of acquiring volume data of the object. For example, when the ultrasound probe 110 has one-dimensional arrangement of elements, the ultrasound probe 110 may acquire volume data in accordance with a Freehand method. Alternatively, the ultrasound probe 110 may acquire volume data by a mechanical method without having a user manipulation. When the ultrasound probe 110 has a two-dimensional arrangement of elements, the ultrasound probe 110 may acquire volume data by controlling the elements.

In particular, when the ultrasound probe 110 receives AC power from an external power supply device or an internal power storage device such as a battery, the plurality of transducer elements vibrate to generate ultrasonic signals. The ultrasonic signals are irradiated to the object, and echo signals reflected by the object are received by the plurality of transducer elements. The plurality of transducer elements vibrate in accordance with the received echo signals, thereby generating current having a frequency corresponding to a vibration frequency.

Referring to FIG. 2, the main body 300 may include a transmit signal generator 210, a beamforming unit (also referred to herein as a "beamformer") 200, a volume data generator 310, a controller 330, a storage unit (also referred to herein as a "storage device" and/or as a "storage") 340, and an image processor 350.

The transmit signal generator 210 may generate a transmit signal in accordance with a control instruction from the controller 330 and transmit the generated transmit signal to the ultrasound probe 110. In this regard, the transmit signal refers to a high-pressure electric signal to vibrate the plurality of transducer elements of the ultrasound probe 110.

The beamforming unit 200, which may perform interconversion between analog signals and digital signals, converts the transmit signals (digital signals) generated by the transmit signal generator 210 into analog signals or converts echo signals (analog signals) received from the ultrasound probe 110 into digital signals which enable communication between the ultrasound probe 110 and the main body 300.

In addition, the beamforming unit 200 may apply time delays to the digital signals in consideration of positions of vibrators and a focal point to overcome a time difference of arrival at the focal point among ultrasonic signals or a time difference of arrival at the transducer elements from the focal point among echo signals.

In particular, under an assumption that a process of concentrating ultrasonic signals, which are simultaneously emitted by the plurality of transducer elements, into a focal point is referred to as focusing, the beamforming unit 200 may perform transmit focusing, by which the ultrasonic signals respectively generated by the transducer elements are sequentially emitted in a predetermined order to remove time difference of arrival at the focal point among the ultrasonic signals, and receive focusing, by which the echo signals are simultaneously aligned at respective transducer elements by using a predetermined time difference to remove time difference of arrival at the transducer elements among the echo signals.

The beamforming unit 200 may be disposed in the main body 300 as illustrated in FIG. 2 or may be installed in the ultrasound probe 110 performing functions thereof.

The volume data generator 310 may generate a plurality of volume data before or while an external stress is applied to the object in response to a plurality of echo signals received in accordance with a plurality of ultrasonic signals transmitted by the ultrasound probe 110. In this regard, the echo signals indicate signals that are processed by executing any of various processes by a signal processing unit (also referred to herein as a "signal processor").

For example, when an echo signal received from an ultrasonic signal transmitted by the ultrasound probe 110 toward the object before an external stress is applied to the object is referred to as a first echo signal, and an echo signal received an ultrasonic signal transmitted by the ultrasound probe 110 toward the object while the external stress is applied to the object is referred to as second echo signal, the volume data generator 310 may generate first volume data corresponding to the first echo signal and second volume data corresponding to the second echo signal.

In this regard, the external stress may be applied to the object using any of a method of applying stress in a proceeding direction of ultrasound, such as a method of applying static pressure by using a hand of an examiner or the ultrasound probe 110, a method of applying high-pressure ultrasound pulse, and a method of applying mechanical vibration, and/or a method of applying stress in a direction perpendicular to the proceeding direction of ultrasound, such as a shearwave method using a transverse wave, without being limited thereto.

In addition, in order to three-dimensionally visualize the object, two-dimensional (2D) cross-sectional images of the object are acquired in response to the echo signals received by the ultrasound probe 110, and the 2D cross-sectional images are sequentially stacked in the corresponding order thereof to generate a set of discrete three-dimensional (3D) alignments. The set of the 3D alignments is volume data.

Figure 3A:
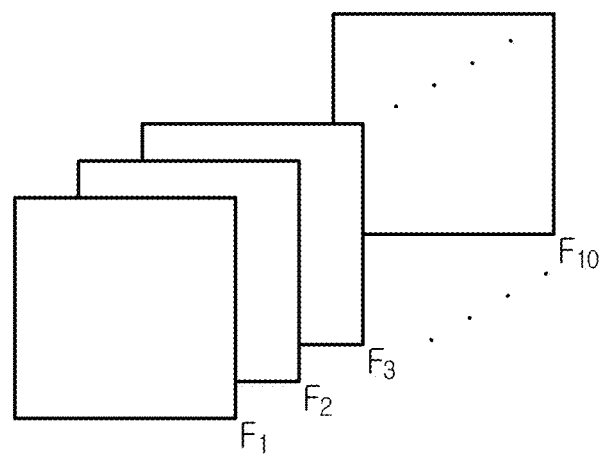
FIG. 3A is a diagram illustrating a plurality of 2D cross-sectional images.
Figure 3B:
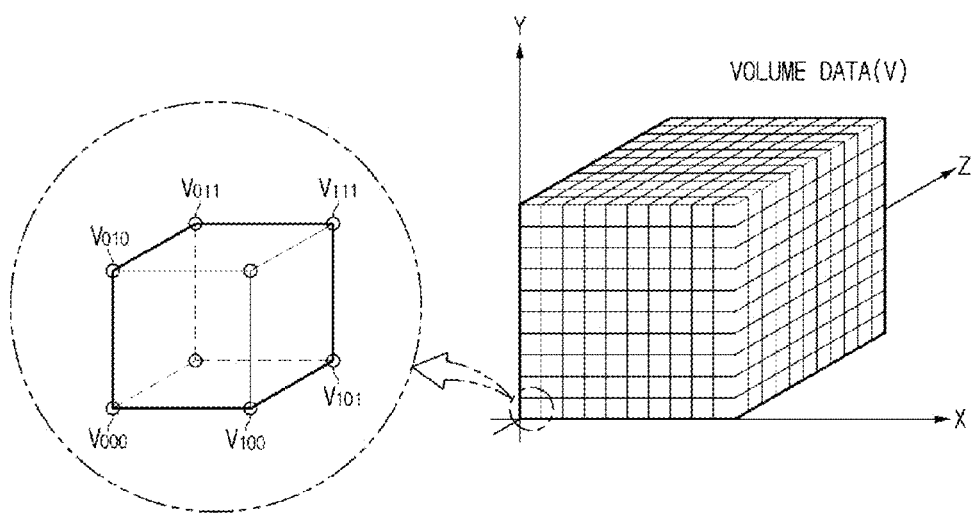
FIG. 3B is a diagram illustrating volume data.

Referring to FIGS. 3A and 3B, an example of a volume data will be described. FIG. 3A is a diagram illustrating a plurality of 2D cross-sectional images. FIG. 3B is a diagram illustrating volume data.

As illustrated in FIG. 3A, a plurality of 2D cross-sectional images F1, F2, F3, . . . , F10 of the object are acquired corresponding to the echo signals received by the ultrasound probe 110. The acquired 2D images F1, F2, F3, . . . , F10 are aligned in a 3D shape in corresponding positions thereof, and data interpolation of the cross-sectional images is performed to generate 3D volume data of the object as illustrated in FIG. 3B.

The volume data may be constituted with a plurality of voxels. The term "voxel" is formed from the terms "volume" and "pixel", and in this aspect, a "voxel" is equivalent to a pixel which has volume (i.e., a 3D version of a pixel). While pixel refers to a single point in a 2D plane, voxel refers to a single point in a 3D space. Thus, a pixel has X and Y coordinates, whereas a voxel has X, Y, and Z coordinates.

Accordingly, when the volume data is referred to as a group V of voxels, and 3D spatial coordinates indicating the position of the voxel are referred to as (x, y, z), the voxel may be represented as $V_{xyz}$.

For example, as illustrated in FIG. 3B, a voxel having spatial coordinates of (0,0,0) may be represented by $V_{000}$, a voxel having spatial coordinates of (1,0,0) may be represented by $V_{100}$, and a voxel having spatial coordinates of (0,1,0) may be represented by $V_{010}$.

In addition, a voxel value va corresponding to a voxel $V_{xyz}$ may be represented by V(x, y, z)=va. Here, the voxel value va may be a scalar value or a vector value, and the volume data may be classified according to the type of the voxel.

For example, a voxel value represented by a binary number of 0 or 1 may be referred to as binary volume data, and a voxel value represented by a measurable value, such as density and temperature, may be referred to as multi-valued volume data. In addition, a voxel value represented by a vector such as speed or RGB color may be referred to as vector volume data.

Optical properties of the voxel, such as opacity values and color values, may be calculated using the voxel values. The opacity value may be calculated using an opacity transfer function that defines the relationship between the voxel values and the opacity values, and the color value may be calculated using a color transfer function that defines the relationship between the voxel values and the color values.

As described above, a plurality of volume data or voxel values generated by the volume data generator 310 may be stored in the storage unit 340. According to an exemplary embodiment, the ultrasound probe 110 may acquire volume data of a brain and the volume data may be stored in the storage unit 340.

As illustrated in FIG. 2, the storage unit 340 may store data or an algorithm to manipulate the ultrasound imaging apparatus.

For example, the storage unit 340 may store a plurality of volume data generated by volume data generator 310. In particular, spatial coordinates of the voxels and voxel values corresponding thereto may be stored.

The storage unit 340 may also store voxel values, opacity values, and color values before and after adjustment by a parameter adjustment unit (also referred to herein as a "parameter adjuster").

The storage unit 340 may also store image data of a result image generated by the image processor 350, which will be described below.

For example, the storage unit 340 may store algorithms, such as, for example, any one or more of an algorithm to generate volume data based on a plurality of 2D cross-sectional images, an algorithm to generate elasticity data based on displacement of the plurality of volume data, an algorithm to align the geometrical positions of the pluralities of volume data and elasticity data in a one-to-one correspondence, an algorithm to adjust the opacity value or the voxel value, an algorithm to adjust the color value, and an algorithm to perform volume rendering based on the volume data.

The storage unit 340 may also store information regarding extraction of a surface region of the object and data regarding a calculated motion vector, which will be described below.

The storage unit 340 may be implemented as any of a storage device including a non-volatile memory device such as a read only memory (ROM), a programmable read only memory (PROM), an erasable programmable read only memory (EPROM), and a flash memory, a volatile memory such as a random access memory (RAM), a hard disk, or an optical disc. However, the exemplary embodiments are not limited thereto, and any other storage units well known in the art may also be used.

The display unit 160 may display an ultrasound image generated by the image processor 350. In particular, the display unit 160 may individually or simultaneously display a cross-sectional image or a 3D image of the object generated by the image processor 350.

In this case, the display unit 160 display a position of an extracted target together with the image. For example, when the ultrasound image displayed in the display unit 160 includes a target, the position of the target may be emphasized in the ultrasound image. In particular, the display unit 160 may display a region of the target by using a different color or shade or may display a boundary of the region of the target by using a different color or shade. Alternatively, the display unit 160 may display a marker indicating the position of the target to the user.

A method of displaying the ultrasound image by the display unit 160 will be described in detail below with reference to the controller 330.

The display unit 160 may also display an ultrasound image generated by frame interpolation according to an exemplary embodiment, which will be described below.

The controller 330 may control the display unit 160 to sequentially display a plurality of cross-sectional images of the object generated by the image processor 350.

In particular, the controller 330 may control the display unit 160 to sequentially display the plurality of cross-sectional images of the object located in a predetermined path in accordance with a predetermined frame rate.

In this regard, the predetermined path refers to not only a linear path but also a curved path or a circular path. The path may be determined by a user input or internal calculation of the ultrasound imaging apparatus.

In addition, a distance between the cross-sectional images of the object and the predetermined frame rate may also be determined by a user input or internal calculation of the ultrasound imaging apparatus.

When the controller 330 controls the display unit 160 to sequentially display the plurality of cross-sectional images of the object, the display unit 160 may also display a position of a target on the cross-sectional images of the object.

In addition, the controller 330 may control a surface region extraction unit (also referred to herein as a "surface region extractor") 400, a motion vector calculation unit (also referred to herein as a "motion vector calculator") 410, an occluded region motion vector calculation unit (also referred to herein as an "occluded region motion vector calculator") 415, a surface region and motion vector tracking unit (also referred to herein as a "surface region and motion vector tracker") 420, and a frame interpolation unit (also referred to herein as a "frame interpolator") 430, which will be described in detail below.

The image processor 350 may generate an ultrasound image of the object by using volume data which relates to the object. In this regard, the image processor 350 may generate not only a 2D ultrasound image of a cross-section of the object but also generate a 3D ultrasound image.

In order to generate a 3D ultrasound image, the image processor 350 may perform volume rendering by using volume data. The image processor 350 may perform volume rendering of the volume data by using any known volume rendering method.

In addition, the image processor 350 may extract a target based on the volume data.

The image processor 350 may be implemented in any of various ways within the technical concept of extracting a target inside the object based on volume data. For example, the image processor 350 may extract a volume data region having a brightness within a predetermined range as a target. Alternatively, the image processor 350 may extract the target by determining whether a size of the volume data region having a predetermined brightness is within a predetermined range.

In addition, the image processor 350 may include a rendering unit (also referred to herein as a "renderer") 351 and an image correction unit (also referred to herein as an "image corrector") 352.

The rendering unit 351 may perform volume rendering based on 3D volume data adjusted by the parameter adjustment unit and generate a projection image of the object. Particularly, the volume rendering is performed on the voxel values, the opacity values, and the color values constituting the volume data generated before the external stress is applied to the object. If there is an adjusted value by the parameter adjustment unit, volume rendering is performed by applying the adjusted value thereto.

A method of performing volume rendering by the rendering unit 351 is not limited. For example, ray casting may be used. Ray casting may be performed by selecting sample points from the first volume data V corresponding to respective pixels of an image, calculating a color value and a transparency value of each of the sample points via interpolation of adjacent voxels, and calculating color values and transparency values of the pixels by accumulating the calculated color values and transparency values.

The image correction unit 352 may correct any one or more of brightness, contrast, color, size, and/or direction of the projection image generated by the rendering unit 351.

The image correction unit 352 may transmit the corrected image to the display unit 160 connected to the main body 300 via a wired or wireless communication network. Accordingly, the examiner may check the corrected result image of the object.

Figure 4:
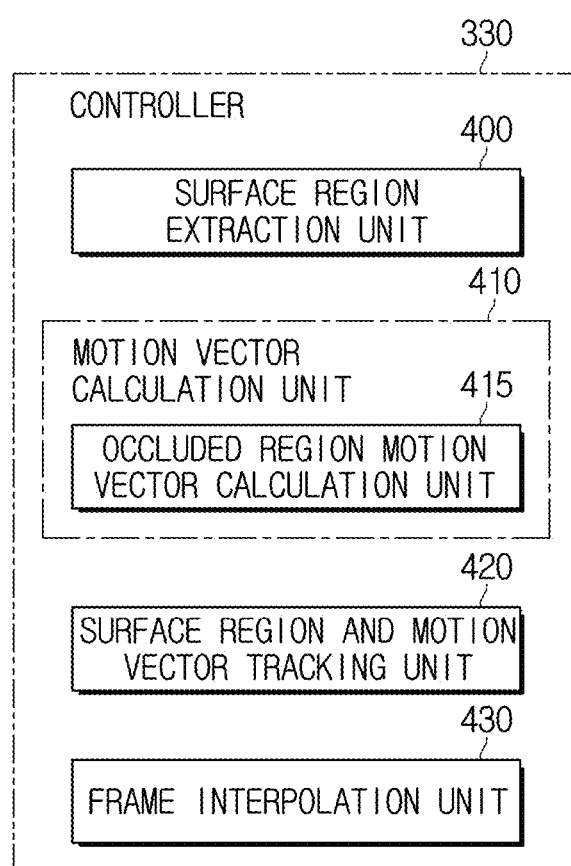
FIG. 4 is a block diagram illustrating a controller of an ultrasound imaging apparatus, according to an exemplary embodiment.

FIG. 4 is a block diagram illustrating the controller 330 of the ultrasound imaging apparatus.

The controller 330 may include and control the surface region extraction unit 400, the motion vector calculation unit 410, the occluded region motion vector calculation unit 415, the surface region and motion vector tracking unit 420, and the frame interpolation unit 430. Operations thereof which are related to an exemplary embodiment will be described in detail with reference to FIGS. 6 and 7.

Figure 5:
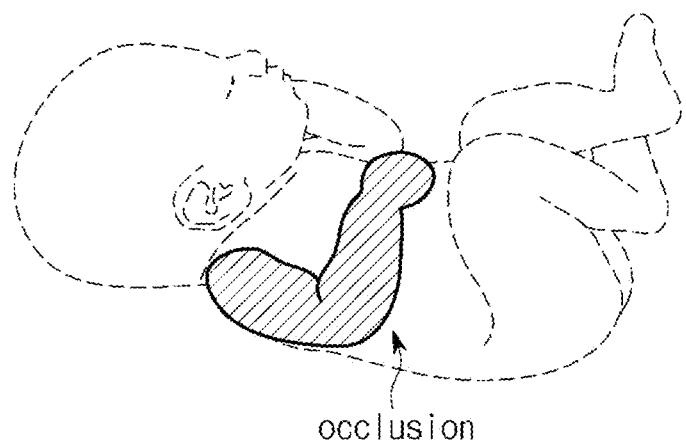
FIG. 5 is a diagram for describing an occluded region that is screened by a motion in a 2D image.

FIG. 5 is a diagram for describing an occluded region that is hidden by motion in a 2D image. FIG. 5 is a schematic diagram of a fetus in an ultrasound image for convenience of explanation.

As illustrated in FIG. 5, when the object is a fetus, an occluded region is generated in a 2D ultrasound image by a motion of the fetus. In FIG. 5, one arm of the fetus is filled with crosshatched lines which indicate an occluded region. The body of the fetus is partially screened by an area corresponding to the arm via the motion of the arm of the fetus. Thus, a portion of the body screened by the arm cannot be identified using the 2D ultrasound image. In this aspect, it is difficult to calculate a motion vector of the occluded portion of the body while calculating the motion vector for frame interpolation.

Figure 6:
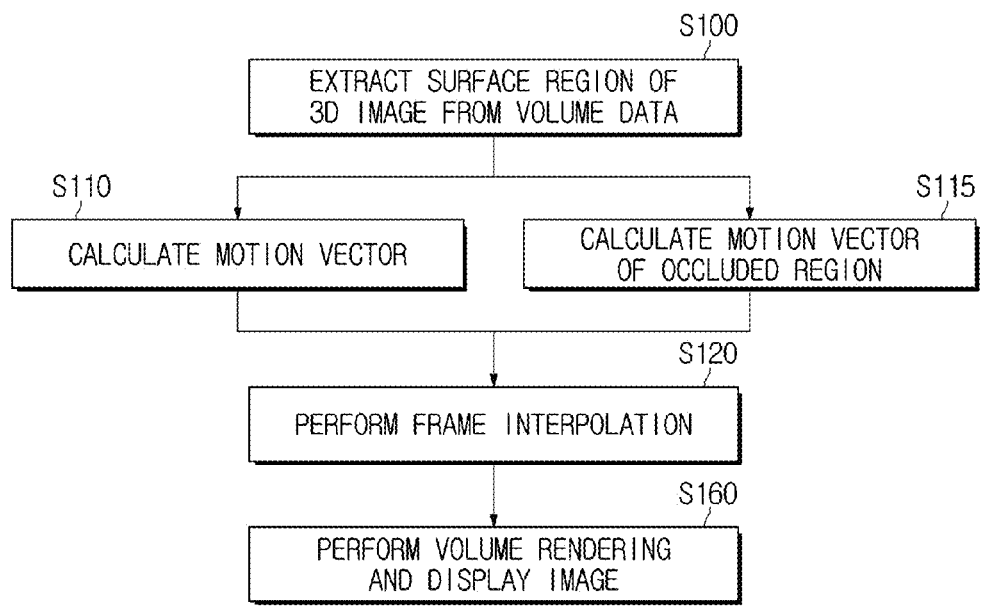
FIG. 6 is a flowchart illustrating a method of controlling an ultrasound imaging apparatus by which a surface region and a motion vector of the next frame are not tracked.
Figure 7:
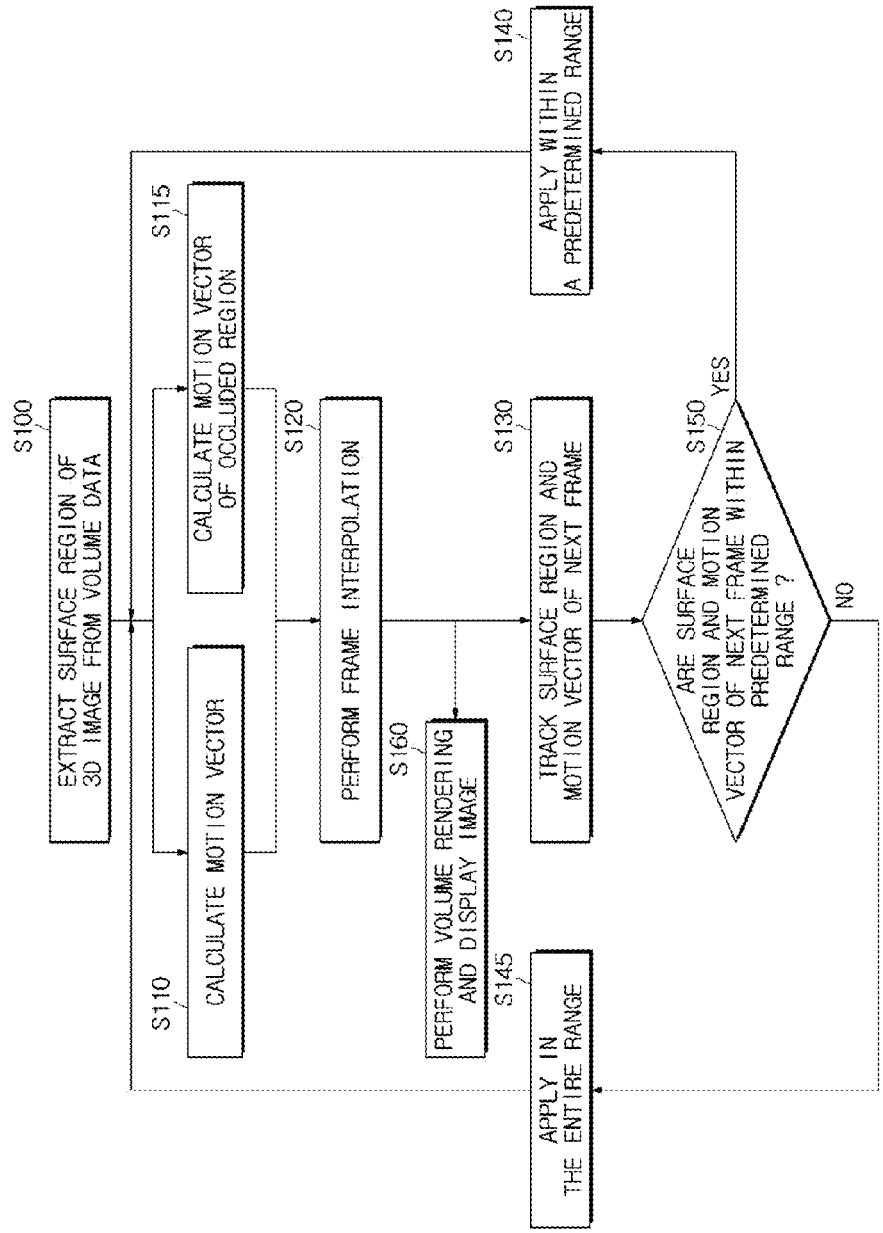
FIG. 7 is a flowchart illustrating a method of controlling an ultrasound imaging apparatus by which a surface region and a motion vector of the next frame are tracked.

FIG. 6 is a flowchart illustrating a method for controlling an ultrasound imaging apparatus by which a surface region and a motion vector of the next frame are not tracked. FIG. 7 is a flowchart illustrating a method for controlling an ultrasound imaging apparatus by which a surface region and a motion vector of the next frame are tracked. Hereinafter, an ultrasound imaging apparatus and a method for controlling the same according to an exemplary embodiment will be described with reference to FIGS. 4 and 8 to 12.

First, as illustrated in FIG. 6, in operation S100, a surface region of a 3D image is extracted from volume data.

Figure 8:
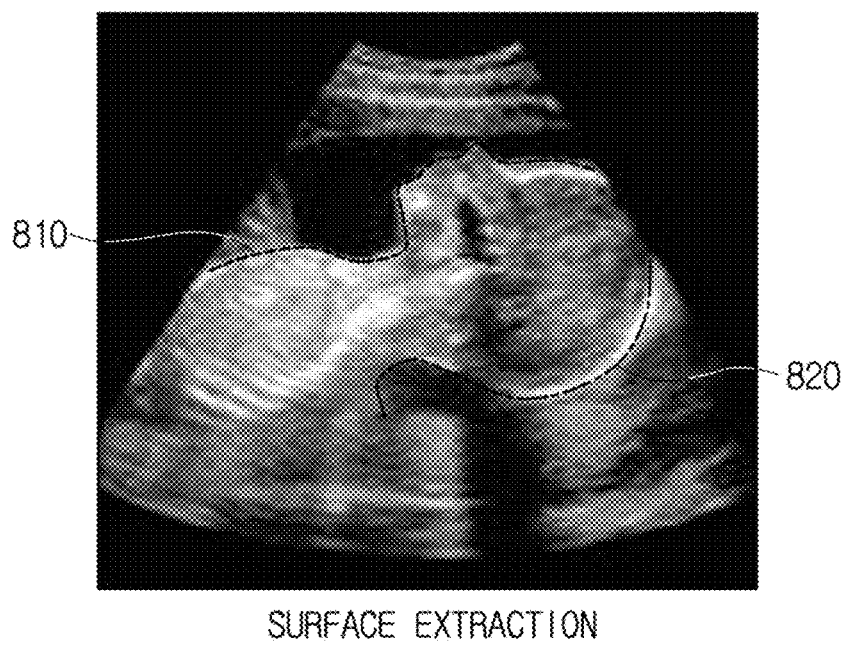
FIG. 8 is an ultrasound image showing a region to extract the surface region of an object, according to an exemplary embodiment.

FIG. 8 is an ultrasound image indicating a surface region to extract a surface region of an object, according to an exemplary embodiment.

As illustrated in FIG. 8, a fetus will be described as the object by way of example. In a 3D ultrasound image, a portion marked by a line 810 may be regarded as a frontal surface region of the fetus. In particular, an outline of the frontal appearance of the fetus is set as the surface region from 3D volume data. It may be understood that an outer surface of the 3D image corresponds to the surface region.

The surface region may be a region of the frontal surface of the fetus as illustrated in FIG. 8. Further, any other regions for setting the surface such as a back surface marked by a line 820 or a side surface may be selected.

As illustrated in FIG. 4, the surface region extraction unit 400 of the controller 330 extracts the surface region of the object. The surface region extraction unit 400 may extract a surface region required to display an image of the object. In particular, the surface region extraction unit 400 extracts the surface region by selecting a region of interest (ROI). A basic method of extracting the surface region entails extracting a desired surface region from volume data by using a virtual camera and displaying the extracted surface region on a screen. In this aspect, a 2D image viewed from the 3D volume data is an image viewed from a predetermined position. In addition, the surface of the fetus may be extracted in the ultrasound image by using support vector machine (SVM)-based texture classification. According to the method of extracting the surface region of the fetus as described above, a fetus region is separated from a 3D ultrasound image in order to obtain a clear image of the fetus which is not screened by impurities and to reduce data volume, since a large amount of abdominal walls or floating materials in amniotic fluid are shown in a 3D ultrasound image together with the fetus. In general, a method of separating a fetus region from the surroundings in a 3D ultrasound image may include selecting a region of interest (ROI), extracting a surface, and performing region division to remove undesired regions. Thus, the extraction method may automatically extract the frontal surface of the fetus from 3D ultrasound volume data by using the SVM-based texture classification.

The surface region extraction unit 400 extracts the surface region of the object as described above. However, extraction of the ROI may be implemented in various ways without limitation.

As illustrated in FIG. 4 and FIG. 6, the motion vector calculation unit 410 of the controller 330 calculates a motion vector in the extracted surface region of the object in accordance with a control by the controller 330 in operation S110.

The motion vector refers to a vector which indicates a speed and a direction of a moving object of interest. According to an exemplary embodiment, the motion vector may be calculated by extracting the surface region from 3D volume data. By using 3D volume data, motion vectors of respective tissues of the object may be calculated. In this case, the motion vector is calculated on the assumption that each tissue of the object linearly moves.

When a first predetermined time is referred to as "t" and a next (i.e., second) predetermined time is referred to as "t+1", a vector indicating the degree of movement of the object from the first predetermined time of t to the next time of t+1, i.e., the degree of volume data change between the first predetermined time of t and the next time of t+1 to overlap each other, is the motion vector.

The motion vector calculation unit 410 calculates the motion vector by comparing volume data which relates to the surface region of the object at the first predetermined time of t and volume data which relates thereto at the next time of t+1 through Equation 1 below.

$$(V_x', V_y', V_z') = \min_{V_x, V_y, V_z} \left( \sum_{(x,y,z) \in S(w)} |I^{t+1}(x+V_x, y+V_y, z+V_z) - I^t(x,y,z)| \right) \quad \text{Equation 1}$$

In Equation 1, S is a surface region of the object, the motion vector of which is desired to be calculated, w is one region (window) of the surface region of volume data, and I is an image of ultrasound volume data. In addition, t is the first predetermined time and t+1 is the next predetermined time as described above, x, y, and z are coordinates of the respective axes of the 3D volume data, $V_x$, $V_y$, and $V_z$ are amounts of movement of the object from the first predetermined time of t to the next time of t+1, and $V_x'$, $V_y'$, and $V_z'$ indicate the motion vector.

Figure 11:
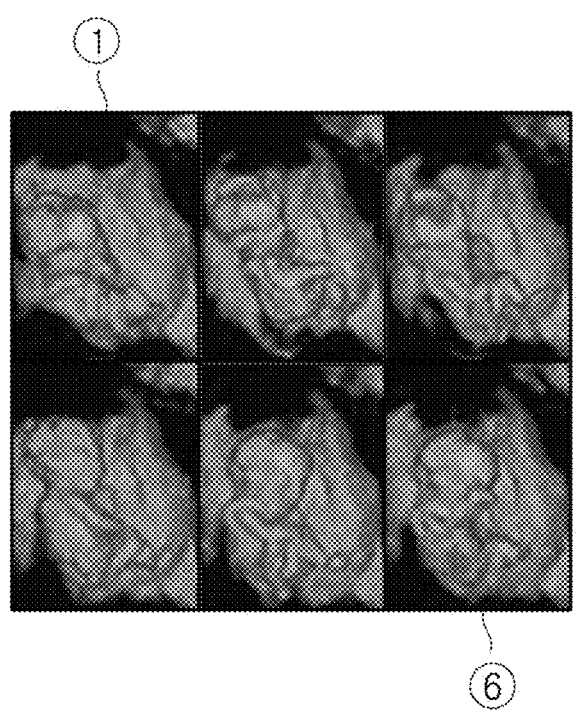
FIG. 11 illustrates ultrasound images indicating frame interpolation at a predetermined time, according to an exemplary embodiment.

FIG. 11 will be described in more detail. FIG. 11 illustrates ultrasound images showing frame interpolation at a predetermined time, according to an exemplary embodiment.

As illustrated in FIG. 11, when image ① is referred to as an ultrasound image at a time of t, and image ⑥ is referred to as an ultrasound image at a time of t+1, frame interpolation is performed after predicting movement of the object by calculating a motion vector between the images ① and ⑥.

In Equation 1, the motion vector of one region w instead of the entire region of a corresponding surface region S (also referred to herein as a "subregion w") of the image is calculated. When the movement from the time of t to the time of t+1 is changed by $V_x$, $V_y$, and $V_z$, a position which has changed from initial coordinates x, y, and z by $V_x$, $V_y$, and $V_z$ is illustrated in an image at the time of t+1. Thus, a motion vector $V_x'$, $V_y'$, and $V_z'$ corresponding to an amount of movement change may be found by calculating a difference between a position which corresponds to the image at the time of t+1 and a position which corresponds to the image at the time of t as a vector difference and adding up the vector difference. As a minute value, the amount of movement change $V_x$, $V_y$, and $V_z$ of the object generated from the time of t to the time of t+1 is calculated to be minimized.

Frame interpolation is performed by forming images between the time of t and the time of t+1 by using the motion vector calculated according to the aforementioned method, and a detailed description thereof will be given below.

While calculating the motion vector, a motion vector of an occluded region is also calculated. As described above with reference to FIG. 5, an occluded region is generated in the extracted surface region of the object according to the motion of the object or change in movement of the object when a 2D image is displayed. In order to perform frame interpolation to which the motion vector of the occluded region is reflected, the motion vector of the occluded region is also calculated.

As illustrated in FIG. 4 and FIG. 6, the occluded region motion vector calculation unit 415 within the motion vector calculation unit 410 is controlled by the controller 330 to calculate the motion vector of the occluded region in operation S115, which will be described with reference to FIGS. 9A and 9B.

Figure 9A:
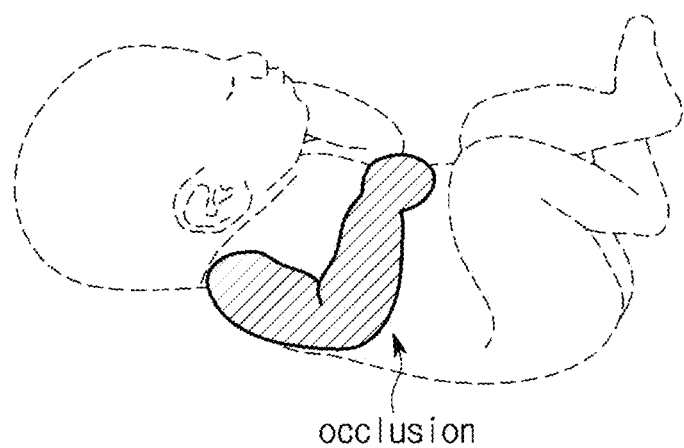
FIGS. 9A and 9B are diagrams for describing a calculation of a motion vector of a surface region of an object having an occluded region.
Figure 9B:
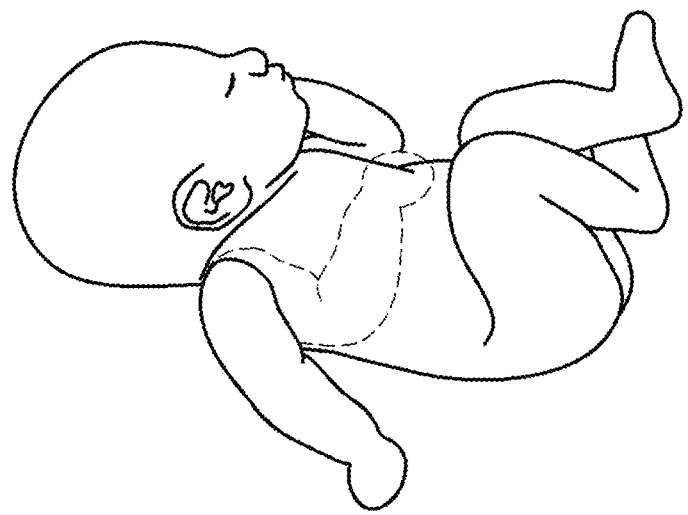

Referring to FIGS. 9A and 9B, an ultrasound image having an occluded region generated at the time of t as described above with reference to FIG. 5 is illustrated in FIG. 9A, and an ultrasound image in which the motion of the object is changed at the time of t+1 is illustrated in FIG. 9B. The occluded region may be extracted from a difference between data at the time of t and data at the time of t+1. In FIG. 9A, since the fetus is putting one arm on the body, an occluded region is caused by the arm with respect to the body. In FIG. 9B, since the fetus is stretching the arm, a motion vector of the body corresponding to the occluded region may be calculated by using the difference between the two ultrasound images.

Hereinafter, the occluded region will be described with reference to Equation 2.

① $S_t = P(I^t)$

② $S_{t+1} = P(I^{t+1})$

③ $S' = XoR(S_t, S_{t+1})$

④ $S_t' = S_t \cup S'$

⑤ $S_{t+1}' = S_{t+1} \cup S'$      Equation 2

In Equation 2, S is a surface region of the object, and S' is an occluded region. Equation 2-① is an equation which relates to an image of ultrasonic volume data in the surface region of the object of the time of t, and Equation 2-② is an equation which relates to an image of ultrasonic volume data in the surface region of the object at the time of t+1. Equation 2-③ is an equation for calculating the occluded region in the surface region by using Equation 2-① and Equation 2-②. An exclusive OR (XoR) region of $S_t$ and $S_{t+1}$ corresponds to the occluded region. Equation 2-④ is an equation for calculating a motion vector of the surface region having an occluded region at the time of t and corresponds to an union of the surface region $S_t$ and the occluded region S'. Equation 2-⑤ is an equation for calculating a motion vector of the surface region having an occluded region at the time of t+1 and corresponds to a union between the surface region $S_{t+1}$ and the occluded region S'. Thus, the motion vector of the occluded region may be calculated by using Equation 2-④ and Equation 2-⑤ as described above with reference to the calculation of the motion vector.

As described above, the motion vector calculation unit 410 and the occluded region motion vector calculation unit 415 calculate the motion vector which includes the motion vector of the occluded region of the object in the ultrasound image based on the extracted surface region of the object, and data which relates to the calculated motion vector may be stored in the storage unit 340, which will be described below.

As illustrated in FIG. 4 and FIG. 6, the frame interpolation unit 430 of the controller 330 performs frame interpolation on the surface region by using the motion vector calculated in the surface region of the object by a control of the controller 330 in operation S120.

FIG. 11 illustrates ultrasound images which indicate a frame interpolation at a predetermined time, according to an exemplary embodiment.

As illustrated in FIG. 11, in ultrasound images of the fetus, the motion vector between the time of t and the time of t+1 is calculated, and frame interpolation is performed between the time of t and the time of t+1. When image ① is referred to as an image at the time of t, and image ⑥ is referred to as an image at the time of t+1, images therebetween are images generated by frame interpolation based on the calculated motion vector. FIG. 11 illustrates a relatively small number of images generated by frame interpolation for convenience of explanation. In actual frame interpolation, more images may be generated, and a relatively short time interval may be used between successive generations of images, thereby generating a natural image.

According to a frame interpolation method according to an exemplary embodiment, a natural real time multifocal ultrasound image may be provided by changing a frame rate by inserting interpolated frames.

According to the frame interpolation method, the frame rate of a final image may be increased by additionally inserting virtual images between two image pairs of different times, thereby providing a natural image, i.e., moving image.

Figure 10A:
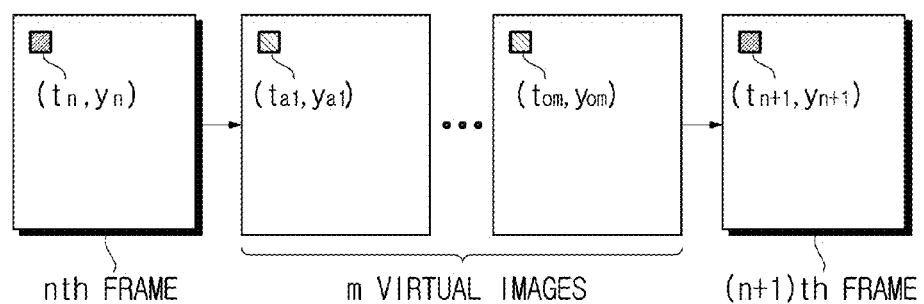
FIG. 10A is a diagram for describing virtual images generated by frame interpolation.

FIG. 10A is a diagram for describing virtual images generated by frame interpolation.

Figure 10B:
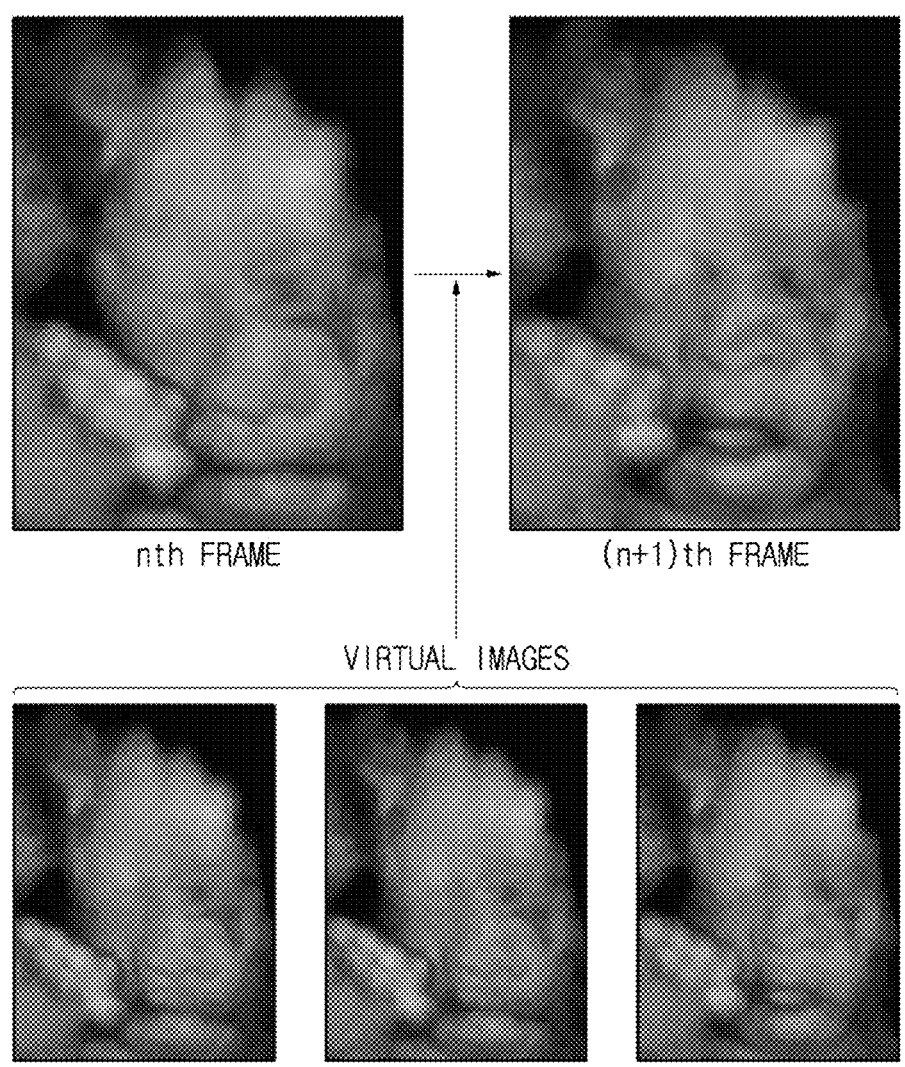
FIG. 10B is an example of virtual images generated by frame interpolation.

FIG. 10A illustrates m virtual images generated by an interpolation method and inserted between an $n^{th}$ frame and an $(n+1)^{th}$ frame among n frames of an image. FIG. 10B illustrates examples of virtual images generated by frame interpolation as described in FIG. 10A. By inserting the generated virtual images between the $n^{th}$ frame and the $(n+1)^{th}$ frame, a motion of the fetus may be naturally displayed.

First, referring to FIG. 10A, when a linear interpolation method is used, a display time of an image at the $n^{th}$ frame and coordinates of a pixel of the image are referred to as ($t_n$, $y_n$), and a display time of an image at the $(n+1)^{th}$ frame and coordinates of a pixel of the image are referred to as ($t_{n+1}$, $y_{n+1}$). In this case, a display time of the $j^{th}$ virtual image and coordinates of a pixel in the image among m virtual images inserted between the $n^{th}$ frame and the $(n+1)^{th}$ frame may be defined as ($t_{aj}$, $y_{aj}$). All data which relates to the m virtual images may be generated by applying an equation which relates to virtual image insertion to all pixels of each of the m virtual images inserted between the $n^{th}$ frame and the $(n+1)^{th}$ frame. The equation is well known in the art, and thus a detailed description thereof will not be given herein.

As illustrated in FIG. 10B, a natural ultrasound image of the fetus may be generated by inserting virtual images between the $n^{th}$ frame and the $(n+1)^{th}$ frame. According to an exemplary embodiment, frame interpolation may be performed by using the calculated motion vector of the surface region of the object.

Hereinafter, frame interpolation will be described with reference to the following equations.

$$\frac{(N-k)*a + k*b}{N} \qquad \text{Equation 3}$$

$$① \quad I^t\left(x + \frac{k}{N}*V_x, y + \frac{k}{N}*V_y, z + \frac{k}{N}*V_z\right) \qquad \text{Equation 4}$$

$$② \quad I^{t+1}\left(x - \frac{(N-k)}{N}*V_x, y - \frac{(N-k)}{N}*V_y, z - \frac{(N-k)}{N}*V_z\right)$$

When $I^t$ is referred to as an image of ultrasonic volume data at the time of t, and $I^{t+1}$ is referred to as an image of ultrasonic volume data at the time of t+1, linear interpolation may be represented by Equation 3.

In Equation 3, N is the number of interpolation steps (the number of images interpolated between the time of t and the time of t+1, i.e., the number of images to be generated), k is an ordinal number of an image among the interpolated images, "a" is image interpolation from the time of t to the time of t+1, and "b" is image interpolation from the time of t+1 to the time of t.

As a motion vector with respect to a variation of the movement of the object with time, a variation at the time of t may be represented by (0, 0, 0), a variation at a time of t+0.5 is may be represented by ($V_x/2$, $V_y/2$, $V_z/2$), and a variation at the time of t+1 may be represented by ($V_x$, $V_y$, $V_z$). Thus, interpolated images of the image of ultrasonic volume data with time may be $I^t(x, y, z)$ at the time of t, $I^t(x+V_x/2, y+V_y/2, z+V_z/2)$ at the time of t+0.5, and $I^t(x+V_x, y+V_y, z+V_z)$ at the time of t+1.

A time interval of the frame interpolation is $\Delta t = k/N$. Here, $\Delta t$ is a very short time which generally falls within a range of between several tens of milliseconds to several hundreds of milliseconds.

After $\Delta t$, general equations of the interpolated image may be represented by Equation 4-① and Equation 4-②. Equation 4-① may be referred to as "a" which indicates image interpolation from the time of t to the time of t+1, and Equation 4-② may be referred to as "b" which indicates image interpolation from the time of t+1 to the time of t.

Thus, an equation for calculating an interpolated image after $\Delta t$ may be obtained by substituting equations of a and b into Equation 3. This may be interpreted as an average between a and b in the linear interpolation.

The frame interpolation unit 430 may perform frame interpolation on the surface region image of the object by using the aforementioned image interpolation method by a control of the controller 330. However, the image interpolation method is not limited thereto, and various other methods may also be used.

Hereinafter, a method of determining a surface region at a predetermined frame by tracking a motion vector of the surface region of the predetermined frame by using data which relates to a calculated motion vector of a surface region with respect to a preceding frame will be described.

FIG. 7 is a flowchart illustrating a method for controlling an ultrasound imaging apparatus by which a surface region and a motion vector of the predetermined frame are tracked. In this aspect, the predetermined frame is referred to herein as the "next" frame because the method entails using data which relates to the preceding frame.

The surface region and motion vector of the next frame are tracked since an amount of calculation increases when the surface region is extracted from volume data at each frame and the motion vector is calculated therefrom. The amount of calculation may be reduced by tracking the surface region and the motion vector of the next frame within a predetermined range based on data stored in the storage unit 340 in operation S130. In particular, a region of the motion vector of the next frame is estimated within the range of the previous motion vector.

As illustrated in FIG. 7, in operation S150, the surface region and motion vector tracking unit 420 in the controller 330 determines whether the surface region and the motion vector of the next frame are within a predetermined (stored) range of the surface region and the motion vector in images generated by frame interpolation performed on the surface region of the volume data of the object by a control of the controller 330. When the surface region and the motion vector of the next frame are within the predetermined range, in operation S140, the motion vector is calculated within the range. In particular, a variation of movement within a range of vector quantities of the motion vector on the previous surface region is calculated as a motion vector. However, when the surface region and the motion vector of the next frame are not within the predetermined range, in operation S145, the motion vector is calculated in the entire range according to the control illustrated in FIG. 6 without considering the range.

As described above, the tracking of the surface region and the motion vector of the next frame is within the scope of the present disclosure and may be optionally applied to exemplary embodiments of the present disclosure.

As described above, the method for controlling the ultrasound imaging apparatus may include extracting a surface region, calculating a motion vector of the surface region, performing frame interpolation by using the calculated motion vector, calculating a motion vector of an occluded region while calculating the motion vector of the surface region, and tracking a surface region and a motion vector of the next frame, as illustrated in FIG. 6 and FIG. 7.

Figure 12:
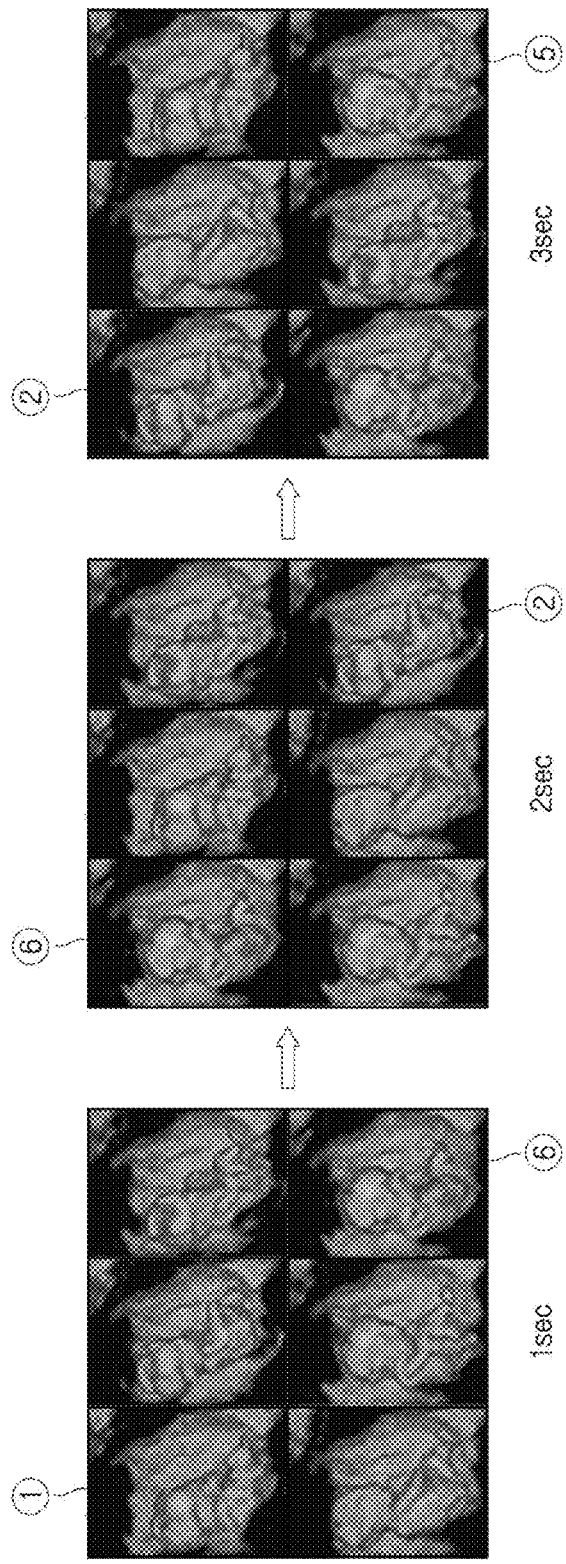
FIG. 12 illustrates ultrasound images indicating frame interpolation at consecutive times, according to an exemplary embodiment.

FIG. 12 illustrates ultrasound images indicating frame interpolation at consecutive times, according to an exemplary embodiment.

In FIG. 12, a time interval between frames is set as 1 second. As illustrated in FIG. 12, frames may be classified into frames at 1 sec, frames at 2 sec, and frames at 3 sec.

At 1 sec, frame interpolation according to an exemplary embodiment is performed between image ① and image ⑥ as described above. At 2 sec, frame interpolation is performed between image ⑥ obtained at 1 sec, as a starting image, and image ②. At 3 sec, frame interpolation is performed between image ② obtained at 2 sec, as a starting image, and image ⑤. Thus, natural images may be generated by frame interpolation performed on the surface region of the object.

As illustrated in FIGS. 6 and 7, after the frame interpolation is performed, in operation S160, the rendering unit 351 of the image processor 350 performs volume rendering, and the generated ultrasound image is displayed on the display unit 160.

According to an exemplary embodiment, the ultrasound imaging apparatus extracting a surface region of an object from volume data, performing frame interpolation on the extracted surface region of the object to calculate a motion vector, and the method of controlling the ultrasound imaging apparatus are described above.

As is apparent from the above description, according to the ultrasound imaging apparatus and the method of controlling the same according to an exemplary embodiment, the occluded region generated in a 2D image may be removed, and the amount of calculation of the motion vector of 3D volume data may be reduced.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. An ultrasound imaging apparatus comprising:
    a volume data generator configured to acquire volume data which relates to an object;
    a surface region extractor configured to extract a surface region of the object based on the acquired volume data; and
    a frame interpolator configured to perform frame interpolation on the extracted surface region of the object.

2. The ultrasound imaging apparatus according to claim 1, further comprising a motion vector calculator configured to calculate a motion vector in the extracted surface region of the object.

3. The ultrasound imaging apparatus according to claim 2, wherein the motion vector calculator comprises an occluded region motion vector calculator configured to calculate a motion vector of an occluded region.

4. The ultrasound imaging apparatus according to claim 3, wherein the occluded region includes a region which corresponds to a time difference between a first predetermined time and a second predetermined time in the surface region of the object.

5. The ultrasound imaging apparatus according to claim 4, wherein the motion vector calculator is further configured to calculate the motion vector by comparing volume data which relates to the first predetermined time with volume data which relates to the second predetermined time.

6. The ultrasound imaging apparatus according to claim 3, wherein the occluded region includes a region generated when the frame interpolation is performed.

7. The ultrasound imaging apparatus according to claim 3, wherein the occluded region motion vector calculator is further configured to calculate the motion vector of the occluded region simultaneously with calculating the motion vector in the surface region of the object.

8. The ultrasound imaging apparatus according to claim 2, wherein the motion vector calculator comprises a surface region and motion vector tracker configured to track a surface region and a motion vector of a predetermined frame.

9. The ultrasound imaging apparatus according to claim 8, wherein the surface region and motion vector tracker is further configured to track the surface region and the motion vector of the predetermined frame based on data which relates to the extracted surface region and the calculated motion vector.

10. The ultrasound imaging apparatus according to claim 2, wherein the motion vector calculator is further configured to calculate a motion vector of a subregion of a frame.

11. The ultrasound imaging apparatus according to claim 1, wherein the surface region extractor is further configured to extract a surface region of at least one from among an outline of a fetus and an organ comprising a heart.

12. A method for controlling an ultrasound imaging apparatus, the method comprising:
acquiring volume data which relates to an object;
extracting a surface region of the object based on the acquired volume data; and
performing frame interpolation on the extracted surface region of the object.

13. The method according to claim 12, further comprising calculating a motion vector in the extracted surface region of the object.

14. The method according to claim 13, wherein the calculating the motion vector comprises calculating a motion vector of an occluded region.

15. The method according to claim 14, wherein the calculating the motion vector of the occluded region is performed simultaneously with calculating the motion vector in the surface region of the object.

16. The method according to claim 13, wherein the calculating the motion vector is performed by calculating a motion vector by comparing volume data which relates to a first predetermined time with volume data which relates to a second predetermined time.

17. The method according to claim 16, wherein the calculating the motion vector in the surface region of the object comprises tracking a surface region and a motion vector of a predetermined frame.

18. The method according to claim 17, wherein the tracking the surface region and the motion vector of the predetermined frame is performed by tracking a surface region and a motion vector of the predetermined frame based on data which relates to the extracted surface region and the calculated motion vector.

19. The method according to claim 13, wherein the calculating the motion vector is performed by calculating a motion vector of a subregion of a frame.

20. The method according to claim 12, wherein the object includes a fetus, and
the extracting the surface region of the object is performed by extracting a surface region of at least one from among an outline of the fetus and an organ comprising a heart.

* * * * *